US008414850B2

United States Patent
Pietzonka et al.

(10) Patent No.: US 8,414,850 B2
(45) Date of Patent: Apr. 9, 2013

(54) PROCESS FOR THE WORKING-UP OF A VITAMIN E- AND VITAMIN E-ACETATE-CONTAINING MIXTURE OR PRODUCT STREAM

(75) Inventors: Werner Pietzonka, Therwil (CH); Peter Ruckstuhl, Hölstein (CH); Angela Wildermann, Bad Säckingen (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/329,853

(22) Filed: Dec. 19, 2011

(65) Prior Publication Data
US 2012/0156107 A1 Jun. 21, 2012

Related U.S. Application Data

(62) Division of application No. 11/659,475, filed as application No. PCT/EP2005/008982 on Aug. 19, 2005, now Pat. No. 8,183,396.

(30) Foreign Application Priority Data

Aug. 19, 2004 (CH) ....................................... 1366/04

(51) Int. Cl.
*B01J 8/00* (2006.01)
*B01D 3/14* (2006.01)
*C07D 311/00* (2006.01)

(52) U.S. Cl. ........ 422/608; 422/610; 422/614; 422/187; 202/154; 202/158; 202/161; 202/162; 261/148; 261/149; 549/408

(58) Field of Classification Search .................. 422/608, 422/610, 614, 187; 202/154, 158, 161, 162; 261/148, 149; 549/408
See application file for complete search history.

(56) References Cited

U.S. PATENT DOCUMENTS

| 5,468,883 | A | 11/1995 | Grafen et al. |
| 5,582,692 | A | 12/1996 | Baird |
| 6,111,117 | A | 8/2000 | Hartmann et al. |
| 6,518,439 | B1 | 2/2003 | Dhainaut et al. |
| 6,554,965 | B1 * | 4/2003 | Hartmann et al. ............ 202/158 |
| 2008/0194846 | A1 | 8/2008 | Herguijuela et al. |

FOREIGN PATENT DOCUMENTS

| DE | 27 43 920 A | 3/1978 |
| DE | 42 08 477 A1 | 9/1993 |
| DE | 197 33 503 A | 2/1999 |
| GB | 867166 | 5/1961 |
| WO | WO 97/02880 | 1/1997 |
| WO | WO 02/42286 A1 | 5/2002 |
| WO | WO 03/011850 A1 | 2/2003 |

OTHER PUBLICATIONS

International Search Report mailed Apr. 11, 2006 in PCT/EP2005/008982.
Written Opinion mailed Apr. 11, 2006 in PCT/EP2005/008982.
Herguijuela et al—U.S. Appl. No. 12/911,200, filed Oct. 25, 2010.

* cited by examiner

*Primary Examiner* — Walter D Griffin
*Assistant Examiner* — Lessanework Seifu
(74) *Attorney, Agent, or Firm* — Nixon & Vanderhye P.C.

(57) ABSTRACT

A rectification column and system for the working-up of a vitamin E (VE)- and/or vitamin E acetate (VEA)-containing product stream includes purification of a vitamin E-containing product stream, acetylation of at least a part of the purified vitamin E and purification of at least a part of the acetylated vitamin E, the purification of vitamin E and vitamin E acetate preferably being effected by distillation, for example rectification.

6 Claims, 2 Drawing Sheets

Figure 1:
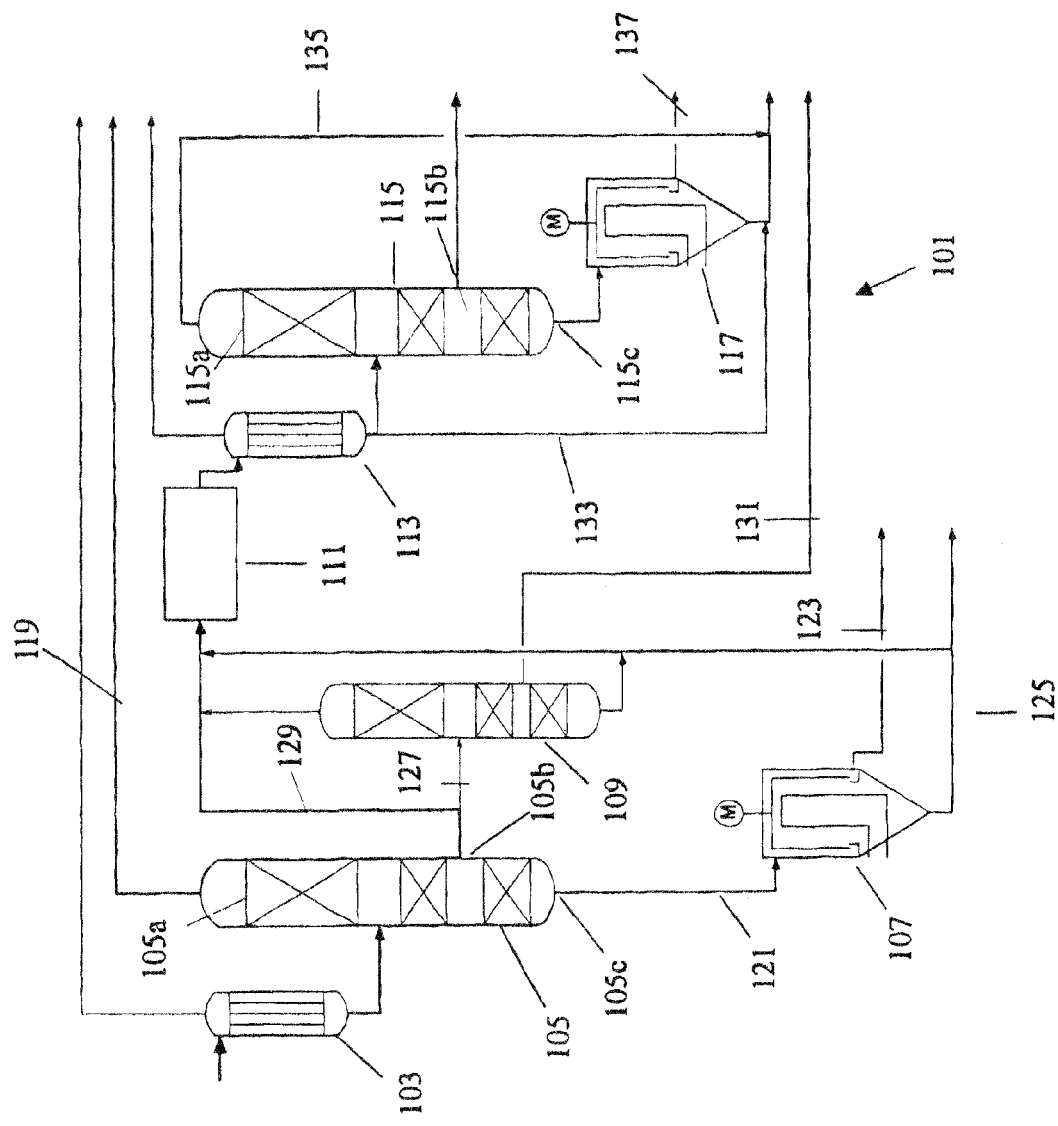

PROCESS FOR THE WORKING-UP OF A VITAMIN E- AND VITAMIN E-ACETATE-CONTAINING MIXTURE OR PRODUCT STREAM

This application is a divisional of commonly owned U.S. application Ser. No. 11/659,475, filed Feb. 6, 2007, now U.S. Pat. No. 8,183,396 which is the national phase application under 35 USC §371 of PCT/EP2005/008982, filed Aug. 19, 2005 which designated the US and claims benefit of CH 01366/04, filed Aug. 19, 2004, the entire contents of each of which are hereby incorporated by reference.

The invention relates to a process for the working-up of a vitamin E (VE)- and vitamin E acetate (VEA)-containing mixture or product stream for separating lower-boiling and higher-boiling impurities from the useful product.

The preparation of VE, also referred to as alpha-tocopherol, is carried out industrially, for example, by condensation of 2,3,5-trimethylhydroquinone with isophytol in the presence of zinc chloride and hydrochloric acid. Processes for the synthesis of 2,3,5-trimethylhydroquinone are described, for example, in the patent specifications and laid-open applications U.S. Pat. No. 4,239,691, U.S. Pat. No. 3,708,505 and DE-A 32 03 487 and DE-A 42 43 461.

Alpha-tocopherol is as a rule esterified by reaction with acetic anhydride to give tocopherol acetate—also referred to as VEA. Processes for the conversion of alpha-tocopherol into tocopherol acetate (acetylation) are disclosed in the laid-open applications EP-A 0 850 937, DE-A 196 03 142 and DE-A 42 08 477. VEA is used inter alia, as an antioxidant and in the area of human and animal nutrition.

The VEA-containing reaction mixture obtained in the esterification—also referred to below as crude VEA—can be freed from the substantial residues of acetic acid and acetic anhydride, for example, by multistage distillation steps in falling-film evaporators, thin-film evaporators, etc. Usually, such a reaction mixture then contains about 94% by weight of VEA, 1-2% by weight of low-boiling substances (chiefly phytadienes), about 2-3% by weight of unspecified isomers of the useful product (VEA) and 1-2% by weight of high-boiling secondary components.

In the industrial purification of a VEA-containing product stream, for example, cascades of short-path evaporators are used. As complete as possible a separation of the low-boiling substances from the product stream flowing to the cascade of short-path evaporators is decisive for the dimensioning and the operation of the short-path evaporators and the vacuum system at the required, very low pressures. A thin-film evaporator usually operated at about 1 mbar and intended for removing the low boilers is therefore connected upstream of the cascade of short-path evaporators. The vapour stream produced in a thin-film evaporator contains substantially phytadienes, vitamin E acetate and residues of acetic acid and acetic anhydride and is virtually completely condensed in a downstream condenser system. Owing to the high content of low boilers, the condensate obtained cannot be further used and is discarded. Because of the position of the phase equilibrium, the proportion of VEA in this vapour stream is about 13% by weight and the loss of VEA is about 2.7%, based on the inflowing amount of VEA. A low boiler fraction of, usually, about 2% by weight remains in the useful product (bottom product of the thin-film evaporator). The bottom product of the thin-film evaporator is fed to the cascade of short-path evaporators, in which the VEA is further enriched by repeated evaporation and condensation.

The process described above and intended for obtaining VEA has the following disadvantages. As already mentioned, a part of the useful product (VEA) passes out of the thin-film evaporator via the gas phase to the downstream condenser system and is finally lost. Furthermore, only parts of the low boilers are separated off in the thin-film evaporator, which is per se a relatively complicated and expensive apparatus, and the rest remains in the useful product and has to be separated off later on by a complicated procedure. At the same time, owing to the incomplete separation of the main product from the byproducts in the respective purification steps, this process also includes recycled streams which have to be fed back to the process by a relatively complicated procedure in order to minimize the losses of useful substance.

Since VEA is being used to an increasing extent for human nutrition and prophylaxis in healthcare, the purity of this product has to meet increasingly high requirements. The VEA quality required for these intended uses, also referred to below as "pharma grade" (PG) quality, must, inter alia, comply with the following specifications:
VEA content $\geq 97.5\%$ by weight
colourless to slightly greenish yellow The VEA obtained from the process described above has a purity (VEA content) of <97% by weight. With a purity of >92% by weight, it fulfils the condition which is set for the so-called "technical grade" (TG) quality of the useful product but not the requirements of a PG quality. For use as a food additive or for medical applications, it must therefore be subjected to further purification steps.

It is known that, in the working up of product mixtures by distillation, the best results are generally obtained when so-called countercurrent distillation (also referred to as rectification) is used, i.e. a special distillation process with countercurrent flow of descending reflux and ascending vapour in rectification columns. It is usual to use columns in which the mixture to be separated is introduced in the middle part of the column, the vapour becomes enriched with more readily volatile components on its way through the column from bottom to top and the reflux becomes enriched with more sparingly volatile components from top to bottom. The transport of material and heat is intensified by elements installed in the column, such as column trays, random packings or structured packings, which ensure a sufficient contact time of the phases and a sufficiently large phase boundary.

It is furthermore known that, for the separation of high-boiling, temperature-sensitive mixtures of substances which require a high separation efficiency, which also includes the VE- and VA-containing mixtures, it is preferable to use rectification columns which have packings composed systematically in a regular geometry and having defined passage regions for countercurrent phases. This is the case in particular because, compared with random packings, regularly structured packings are distinguished by a higher load capacity and a better separation effect, have a smaller specific pressure drop and require a smaller volume of packings and therefore also permit a smaller mass and heat transfer height. Structured packings are therefore used in all vacuum rectifications, in which, owing to the temperature sensitivity of the mixture to be separated, a limitation of the column pressure drop is particularly important. Column packings known for this intended use are, for example, metal fabric packings of the BX and CY type from Sulzer, expanded metal packings of the Optiflow or Mellapak type and Rhombopak type from Sulzer and Kühni, respectively, and similarly effective metal fabric packings from other companies, such as Montz GmbH.

The rectification of a VEA-containing mixture is disclosed, for example, in WO 97/02880. However, the rectification generally advantageous for the purification of products on an industrial scale presents major problems in this case owing to the high boiling point of VEA and its decomposability at higher temperatures. Substantially distillation under high vacuum or even molecular distillations are therefore carried out in order to be able to distil VEA at as low temperatures as possible.

In spite of the use of the high vacuum, in general only purities of 97.3% (DE-A 27 43 926), 98% (DE-A 42 08 477 and JP-B-58 011 869), 98.5% (U.S. Pat. No. 3,459,773) or 98.5 to 99% (DE-A 21 60 103) are achieved according to the prior art. Purities above 99% were achieved only by molecular distillation, namely purities of 99.3% according to JP-A 51/14671 and 99.5% according to JP-A-62/226976, it being necessary to point out that, on investigation by the more precise methods of analysis used today and with the use of purer comparative substances, presumably lower purity values would be achieved. In addition, the distillation yields achievable in this manner are in each case very low, and both the capital costs and the ongoing operating costs of such plants are therefore very high owing to the extreme complexity.

The processes described above furthermore have the disadvantage that they permit an optionally controllable and variable working-up of crude VE or crude VEA only to a limited extent to give the corresponding end products. In the VE and VEA stages, end products are understood here as meaning the "technical grade" quality VE-TG or VEA-TG and the "pharma grade" quality VE-PG or VEA-PG. The object of the invention is to provide a process for the working-up of a VE- or VEA-containing product stream, which does not have the above-mentioned disadvantages and which permits an economical method, which is simple in terms of process engineering, for separating off VE or VEA with high purity and high yield. In addition, the process should also permit the use of separation apparatuses simple in terms of process engineering and make it possible to prepare optionally all four end products in different and optionally variable proportions. Particularly for the last-mentioned case, it is intended to develop a process which substantially simplifies the working-up process to give the end products VEA-TG, VEA-PG, VE-TG and VE-PG. It is also considered advantageous to develop a process without recycling for the gentler treatment of the products.

The object is achieved by a process having the features of Patent Claim 1.

Advantageous embodiments of the invention form the subject of the dependent Claims.

Claim 1 proposes a process for the working-up of a VE- and VEA-containing product stream, which is substantially characterized by purification of a vitamin E-containing product stream, acetylation of at least part of the purified vitamin E and purification of at least a part of the acetylated vitamin E, the purification of vitamin E and vitamin E acetate preferably being effected by distillation, for example rectification.

According to the invention, a completely novel concept for the purification of VE and VEA products was developed. The VE required for the preparation of VEA is purified prior to the acetylation. This makes it possible to design the entire process concept in such a way that optionally the four end products VEA-TG, VEA-PG, VE-TG and VE-PG can be prepared in different and optionally variable proportions by the process according to the invention, and the working-up process to give the end products can be substantially simplified.

A preferred process according to the invention is characterized in that a vitamin E-containing product stream is fed to a first rectification column, low-boiling products and unspecified isomers of vitamin E being taken off at the top of this first rectification column virtually without loss of useful substance, and a purified, vitamin E-containing stream being taken off at the side and/or at the bottom of the rectification column, at least a part of the side take-off or of the bottom take-off or at least a part of the side and bottom take-off being passed into an acetylation stage for the acetylation of vitamin at least a part of the product stream emerging from the acetylation stage being passed into a second rectification column or being taken off as useful product having a purity of ≧92% by weight, and in a second rectification column, the useful product being obtained as a side take-off having a purity of ≧97% by weight.

In this preferred design of the process according to the invention, only pure waste streams (low boilers, i.e. streams of low-boiling substances/streams comprising unspecified isomers of the useful product/streams of high-boiling byproducts, in each case having very low VE or VEA content) and pure product streams form. Thus, no streams which require further working up are produced, which also permits the elimination of disadvantageous recycling. According to the invention, the rectification columns have structured packings with a ratio of separation efficiency to pressure drop of, preferably, >15 theoretical plates per mbar of pressure drop (basis: F factor=1 $Pa^{0.5}$, column diameter 1 metre, test mixture cis-/trans-decalin). A particularly suitable packing is the OFTIFLOW packing from Sulzer AG. According to the invention, at least the side take-off is effected at the second column by partial condensation in a manner such that the product to be separated off leaves the column as condensate and not as product stream in vapour form. For this purpose, the column incorporates important design details which are important for the partial condensation.

The advantages of the preferred process are the following:

A sharp separation in one column is achieved. Usually, a plurality of columns is required for this purpose.

In particular, the first column has a high separation efficiency in combination with a small pressure drop.

The losses of products are very small.

The purity of the pharma grade products is very high with a content of ≧97% by weight.

The process is very flexible with regard to the amounts of product in PG or TG quality.

In a further preferred embodiment of the invention, before crude VE is fed to the first column or crude VEA is fed to the second column, the product stream is passed, for degassing, into a falling-film evaporator in which in particular low-boiling substances, such as, for example, solvent residues, are removed. Here, the falling-film evaporator can also be designed in such a way that it also serves for reducing the total chlorine content in the crude VE, in order thus to avoid disadvantageous corrosion in the following stages.

The invention is explained in more detail below with reference to the drawing.

Figure 2:
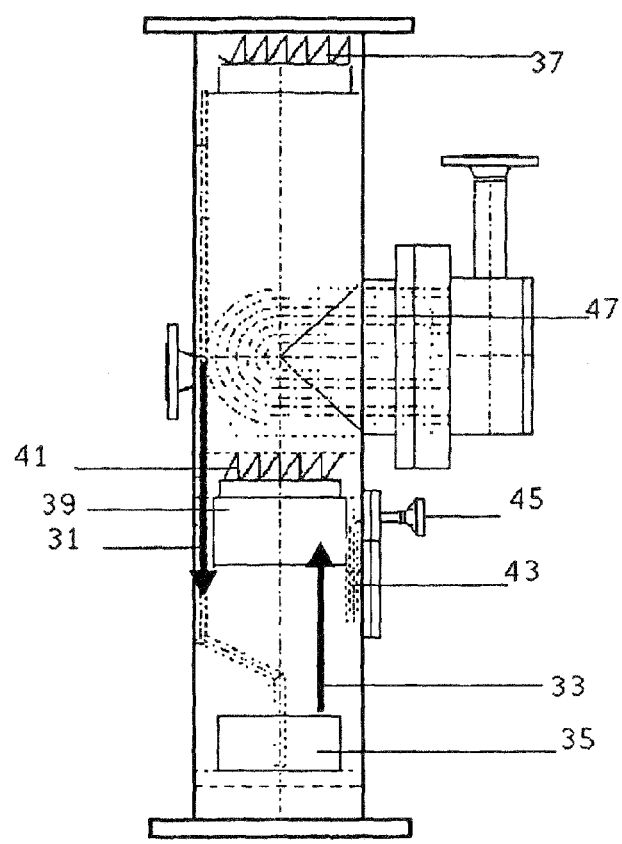

In the drawing,

FIG. 1 shows a schematic diagram of the preferred process according to the invention, and FIG. 2 shows a side take-off point as provided in the first and second and, if required, third rectification column.

In summary, the procedure shown in FIG. 1 for the preparation of VE and VEA in TG and PG quality is organized as follows.

1. First part-stage, consisting of VE degasser, 1st rectification column and VE short-path evaporator:

VE degasser (falling-film evaporator) 103, in particular for separating off low-boiling components, such as solvent residues.

Rectification column 105 for further separation of low-boiling components and for separation of unspecified isomers of the useful product at the top, and for VE side take-off and separation of high-boiling components at the bottom.

Short-path evaporator 107 for separating off residues of the bottom fraction with preparation of the product VE-TG.

2. VE "pharma grade" rectification stage with column 109, optionally only a part of the side takeoff from the column 105 or a part of the side take-off from the column 105 together with a part of the distillate from the short-path evaporator 107 being used for the rectification to give the product VE-PG.

3. Acetylation stage 111, continuously or by the batch process, without a catalyst or, for example, by means of a catalyst, for example pyridine.

4. Second part-stage consisting of degasser, 2nd rectification column and short-path evaporator:

VEA degasser (falling-film evaporator) 113 for separating off the remaining low-boiling components.

2nd rectification column 115 with VEA-PG as side take-off and separation of high-boiling components at the bottom.

Short-path evaporator 117 for separating off residues of the bottom fraction.

In the case of 100% split in favour of the preparation of VEA-TG, the bottom product of the falling-film evaporator 113 corresponds to VEA-TG. At a lower split ratio of TG to PG, the VEA-TG forms as a mixture of the top product of the column 115, the distillate emerging from the short-path evaporator 117 and optionally the bottom product of the falling-film evaporator 113.

For carrying out the process generally:

The product stream containing crude VE is degassed in the falling-film evaporator 103 at about 185° C. and under a vacuum of about 3 mbar. Remaining traces of solvent from the preceding stage (for example toluene, heptane, etc.) are removed. If the falling-film evaporator also has a certain minimum residence time in addition to the circulation of the product stream, it can be used not only for removal of readily volatile components by degassing but also for reduction of the total chlorine content if this is useful for the process and advantageous.

The degassed VE product stream is then added as feed to the first rectification column 105. There, further low-boiling components and also unspecified isomers of the useful product are separated off at the top 105a, in the direction 119 of the arrow. Here, the VE content of the top take-off should be as low as possible in order to limit the VE loss. The loss of the useful product VE via the top take-off of the first rectification column 105 is <5%, preferably <1% and ideally <0.5%, based on that amount of VE in the feed which is added to the column per unit time. As a rule, the largest stream is taken off from the column at the side take-off 105b. Finally, a mixture of high-boiling substances and VE is taken off at the bottom 105c of the column 105 in the direction 121.

The first column 105 is very important for the working-up process. It is here that the magnitude of the maximum proportion (and also the quality) of VEA-PG is specified, since it is only in this column that the low-boiling components and the unspecified isomers of the useful product are separated off and thus discharged from the process. The main requirement regarding the column 105 is thus the removal of the low-boiling components and of the unspecified isomers of the useful product at the top 105a as free of VE as possible. When the process is carried out optimally, the VE loss can be limited to <0.2% by weight, based on the VE contained in the feed.

The low-boiling components can be separated off relatively easily and have a boiling point well below that of VE. These include, for example, the group consisting of the phytadienes or phytenes. Separating off the unspecified isomers of the useful product requires substantially more effort. The high-boiling components on the other hand are once again relatively easy to separate off.

According to the invention, the column 105 is operated as follows:

The side take-off comprises about 75% by weight, based on the added feed stream, said take-off having as high a VE content as possible and containing a small amount of unspecified isomers of the useful product and high-boiling components.

The top take-off comprises about 2 to 4% by weight, based on the feed stream.

The top condenser arranged in the head 105a virtually completely condenses the ascending vapour stream to give reflux and top take-off.

The pressure at the top of the column is preferably about 0.5 to 1 mbar and is kept as constant as possible, and the column temperatures are between 200° C. and 280° C., depending on the loading of the column. While maintaining these guide parameters, and depending on the chosen reflux ratio of the column 105, the latter can be operated so that the VE content in the side take-off is well above 95% by weight and that in the top take-off is substantially below 20% by weight.

The evaporator not shown in detail and present in the bottom 105c of the column 105 is furthermore set up so that it produces the amount of process vapour corresponding to the side take-off and the chosen reflux ratio. For separating off the low-boiling components and the unspecified isomers of the useful product at the top of the column, reflux regulation or take-off regulation in the form of cascade regulation via a temperature in the upper part of the column can, if required, additionally be provided.

The bottom stream of the column 105 is then fed to the short-path evaporator 107 in order to separate the high-boiling substances from the product stream in the direction 123 of the arrow, with as small a VE loss as possible (less than 0.1%, based on VE in the feed to the rectification column 105). The distillate of the short-path evaporator 107 which is removed in the direction 125 can be removed from the plant 101 as product VE-TG having a purity of >92% by weight and/or fed together with the side take-off stream of the first column 105 to the acetylation stage 111.

As a rule, more distillate than required as VE-TG forms in the process, so that the greater part of the distillate of the short-path evaporator 107 is fed to the acetylation. The side take-off of the column 105 can optionally be fed in the direction 127 of the arrow to a further rectification stage and/or in the direction 129 to the acetylation stage 111. The latter is not described in detail here since it is generally known to a person skilled in the art and requires no special adaptations in the context of the invention. In addition, the same also applies to the short-path evaporator 107.

By means of the second rectification in the column 109, it is possible to prepare the product VE-PG. The latter is virtually colourless, has a purity of >97% by weight and is removed from the plant 101 by means of a partial condenser as side take-off in the direction 131 of the arrow. In this case, top take-off and bottom take-off can be fed back to the acetylation stage 111.

The column 109 is designed substantially in the same way as the column 105 or 115 but has smaller dimensions owing to smaller product streams.

There is also the possibility per se of operating the column 109 so that VE-PG can be removed from the column as a bottom take-off. In this case, however, the quality is lower than in the case of the side take-off, owing to a slight coloration of the product.

The product streams obtained as a side take-off of the column 105, as a distillate of the short-path evaporator 107 or as bottom and top product of the column 109 are mixed and are fed to the acetylation stage 111. The mixture substantially having the purity of VE "TG" is reacted with acetic anhydride (AAH) and optionally in the presence of a catalyst to give tocopherol acetate (crude VEA) and acetic acid (AA).

The crude VEA is preferably degassed in the falling-film evaporator 113 at about 185° C. and under a vacuum of 2 mbar. More readily volatile components from the preceding stage (for example acetic acid, acetic anhydride) are removed thereby. VEA having a purity of >92% is obtained at the bottom of the falling-film evaporator 113. The product of the falling-film evaporator 113 already fulfils the specifications for the technical quality of VEA and can therefore be taken off from the plant as VEA-TG via the process line 133.

For the preparation of VEA-PG, the degassed VEA is added as feed to the second rectification column 115. There, the VEA-PG is removed at the side take-off 115b and, according to the specifications applicable today, has a purity of >97%, but preferably of at least 97.5%, and is virtually colourless.

At the top 115a of the column 115, a mixture of VEA and unspecified isomers of the useful product is separated off and is mixed, in the direction 135 of the arrow, with the distillate stream of the short-path evaporator 117 and optionally with the product stream of the evaporator 113. Here, the top take-off preferably comprises about 5%, based on the feed stream added to the column 115.

At the bottom 115c of the column 115, a mixture of VEA and a small amount of high-boiling components is taken off. This mixture is finally fed to the short-path evaporator 117 in order to separate off the high-boiling components in the direction 137 of the arrow (with as low a VEA loss as possible). The distillate of the short-path evaporator 117 together with the top take-off of the column 115 and optionally that proportion of the product of the falling-film evaporator 113 which is not added to the column 115 finally forms—as already mentioned—the VEA-TG.

Both falling-film evaporator 113 and column 115 are formed in substantially the same manner as the two analogous apparatus parts 103 and 105, respectively, above.

In the short-path evaporator 117, the bottom product from the second column 115 is—as already mentioned—further separated. For example, a high-boiling residue containing about 10% of VEA and a distillate containing about 95-96% of VEA are obtained. Here, the VEA loss via the residue is preferably less than 0.1%, based on the VEA in the feed of the column 115, since the distillate ratio D/F is very high.

In a particularly preferred development of the plant, the columns 105 and 115 and, if required, also the column 109 are provided with an Optiflow packing (Sulzer Optiflow C36). Furthermore, all three columns each possess a condenser arranged in the top and an evaporator provided in the bottom. These conventional components which are customary for rectification columns are generally known to a person skilled in the art and are therefore neither described in detail nor shown in the drawing.

The VEA working-up stage according to the invention has therefore proved to be very rugged and economical. Investigations have shown that the VEA-PG removed as a side take-off has a VEA content of $\geq 97.5\%$. Furthermore, it should be mentioned in this context that only a single waste stream is obtained in the entire VEA working-up to give VEA-TG and VEA-PG. This is the residue 137 from the short-path evaporator 117, which, however, has a very low flow rate. If the VEA content in this stream is about 10%, the VEA loss of this entire VEA working-up stage is less than 0.1%, based on the VEA in the feed to the second column.

Regarding the preparation of the two product qualities VEA-TG and VEA-PG, according to the invention various splits of the feed stream are possible, for example the following:

The maximum proportion of VEA-PG is 60% to 75% of PG, thus corresponding to 40% to 25% of TG (i.e. 60% PG:40% TG split or 75% PG:25% TG The minimum proportion of VEA-PG is 0%, corresponding to 100% of VEA-TG, so that in this case the second column 115 is not operated. In the falling-film evaporator 113, the remaining low-boiling components originating from the acetylation, such as, for example, acetic acid (AA) and acetic anhydride (RAH) are removed. The bottom stream from the falling-film evaporator 113 corresponds to the specifications for VEA-TG, corresponding to the 100% split.

The side take-off by partial condensation at least in the column 115, preferably additionally in the column 105 and if required, in the column 109, is decisive with regard to carrying out the process according to the invention. This side take-off will therefore be explained in more detail before the purification of VE and VEA is described in even more detail with reference to a specific example.

In the section of the two rectification columns 105, 115 and 109 according to the invention, shown in FIG. 2, the countercurrent flow is characterized by the descending reflux stream 31 and ascending vapour stream 33 in the rectification column, in the region of the side take-off point the vapour flowing through the packings and separation elements of the side take-off from bottom to top and the reflux flowing inside a guide tube from top to bottom.

A distributor 35 which redistributes the reflux from the collector bed 37 above the side take-off is present in the lower region of the side take-off point. In order to avoid contamination of the side take-off (in vapour form) with liquid, a half layer of Mellapak 250X is furthermore installed as splash guard 39. Directly above this layer 39, the collector 41 for the side take-off is provided. The collector 41 empties, for example, into a trap 43 which opens into an outlet 45 intended for removal of the vapour condensate to be separated off. Above the collector 41 there follows a side take-off partial condenser 47 which, for example, is in the form of a U-tube bundle heat exchanger and serves for producing the vapour condensate. A total take-off collector 37 which transports the reflux—as already mentioned—from the upper part of the side take-off point past the partial condenser 47 into the lower distributor 35 is preferably present as the uppermost element. It is advantageous that the collector 37 carries out a total take-off so that the side take-off is not contaminated by the reflux and the colour of the side take-off is not adversely affected.

According to the invention, the side take-off is effected by partial condensation of the vapour phase ascending in the column. This has the advantage that a vapour condensate, i.e. not a product stream in vapour form, is removed as a side take-off, with the result that the pressure drop caused by the take-off and owing to the smaller volume streams of liquids can be significantly reduced. Since the take-off involves the partial condensation, an additional purification stage is furthermore obtained, which has moreover proved to be particularly advantageous.

It should also be pointed out here that the process described with reference to FIG. 1 represents only one embodiment of the invention and that in particular the development of the plant 101 serving for carrying out the process can be varied in different respects within the scope of protection defined by Claim 1. Thus, for example, it is possible to simplify the plant 101 in such a way that only the preparation of VEA products and, if required, the working-up of VE-TG are possible, so that accordingly the column 109 can be dispensed with. Furthermore, the partial side take-off, as described above, can be used for the purification of VE and VEA independently of the process according to the invention. The partial side take-off can of course also be used for working up or purifying other substances which, like VE and VEA, are high-boiling and temperature-sensitive and are usually purified by means of rectification columns.

The process described above with reference to FIGS. 1 and 2 will now be described in detail by means of a specific example.

Synthetically prepared crude VE containing about 92 to 94% of VE, 1-2% of low-boiling substances (chiefly phytadienes), about 2-3% of unspecified isomers of the useful product VE and about 1-2% of high-boiling components is degassed in a falling-film evaporator at 185° C. and about 3 mbar. The degassed crude VE is fed at a temperature between 180 and 250° C. approximately to the middle of the rectification column 105 having a packing height of 6 to 8 in of the Sulzer Optiflow C36 type. The pressure at the top of the column is 0.5 to 1 mbar. At the top of the column, about 2 to 4% of the feed stream are removed as a top take-off containing about 3% of VE. The column is operated at a reflux ratio of about 10 to 20. The side take-off point is about 2 to 3 in of packing height below the feed inflow point. At the side take-off, about 75% of the feed stream having a VE content of about 97% are removed. The desired flow rate is established by regulation of the partial condenser forward flow temperature. The product obtained at the bottom of the column at a temperature of 260 to 270° C. still contains about 80-84% of VE. This bottom product is now fed to a short-path evaporator, which is operated at a pressure of about 0.1 to 0.2 mbar. The residue still contains about 2-5% of VE, while the VE content in the distillate is more than 92%. The loss of VE via the top take-off of the column and the residue of the short-path evaporator is less than 0.3%, based on the VE in the feed of the column.

A part of the side take-off stream of the column 105 or a part of the mixture of side take-off and distillate of the VE short-path evaporator having a VE content >95% can be fed to the VE "pharma grade" rectification column 109 at a temperature between 180 and 250° C., approximately in the middle of the column with a packing height of 6 to 8 in of the Sulzer Optiflow C36 type. The pressure at the top of the column is 0.5 to 1 mbar. At the top of the column, about 5 to 15% of the feed stream are removed as top take-off having a content of 80 to 90% of VE. The column is operated at a reflux ratio of about 3-5. The side take-off point is about 2 to 3 m of packing height below the feed inflow point. At the side take-off, about 60% of the feed stream having a VE content of more than 98% are removed. The desired flow rate is established by regulation of the partial condenser forward flow temperature.

The product obtained at the bottom of the column at a temperature of 260 to 270° C. still contains about 95 to 97% of VE and is added, together with the top take-off, to the mixture for acetylation.

After the acetylation of the VE-containing mixture comprising side take-off of the column 105, the distillate of the short-path evaporator 107 and optionally of the top and bottom product of the column 109 and the removal of the main part of readily volatile components, such as, for example, acetic acid and acetic anhydride, the crude VEA is degassed in a falling-film evaporator at 185° C. and a pressure of about 2 mbar. VEA which has a content of more than 92% and already fulfils the specifications for the technical quality of VEA (VEA-TG) is obtained at the bottom of the falling-film evaporator.

The degassed VEA is fed at a temperature between 180 and 250° C. approximately to the middle of the rectification column 115 having a packing height of 6 to 8 in of the Sulzer Optiflow C36 type. Usually, the VEA content in the feed stream to the column 115 is about 96%. The pressure at the top of the column is 0.5 to 1 mbar. At the top of the column, about 5% of the feed stream are removed as top take-off having a content of about 80% of VEA. The column is operated at a reflux ratio of about 15 to 30. The side take-off point is about 2 to 3 m of packing height below the feed inflow point. At the side take-off, between 40 and 75% of the feed stream having a VE content of more than 97% are removed, depending on the desired amount of VEA-PG. The desired flow rate is established by regulation of the partial condenser forward flow temperature. The product obtained at the bottom of the column at a temperature of 260 to 270° C. still contains about 90-95% of VEA, depending on the split ratio set. This bottom product is now fed to the VEA short-path evaporator, which is operated at a pressure of about 0.1 to 0.2 mbar. The residue still contains about 10% of VEA, while the VEA content in the distillate is 95 to 96%. The loss of VEA by the residue of the VEA short-path evaporator is less than 0.1%, based on the VEA in the feed stream to the column 115, since the distillate ratio is very high (about 97%). VEA-TG is obtained as a mixture of the top take-off of the column 115, the distillate of the VEA short-path evaporator and (depending on the desired split ratio between VEA-PG and VEA-TG) optionally a part of the feed stream for the column 115. By means of this process, it is possible to vary the ratio of VEA-PG to VEA-TG between 0% of PG (corresponding to 100% of TG) and 75% of PG (corresponding to 25% of TG).

The invention claimed is:

1. A rectification column for working up of vitamin E, comprising:
   a descending reflux stream and ascending vapour stream in the rectification column;
   packings installed in the column for intensifying mass and heat transport, and
   a side take-off section which includes a side take-off location; wherein
   the side take-off section comprises:
   (i) a product stream distributor which redistributes reflux;
   (ii) a splash guard above the product stream distributor;
   (iii) a lateral vapour condensate outlet for the side take-off location;
   (iv) a product stream collector for the side take-off location which opens into the lateral vapour condensate outlet;
   (v) a side take-off partial condenser arranged above the product stream collector, and (vi) a collector bed above the side take-off partial condenser.

2. A rectification column according to claim 1, wherein the collector bed is a total take-off collector.

3. A system for working-up of vitamin E comprising:
(a) a first rectification column according to claim 1 for receiving a vitamin E-containing product stream purifying a vitamin E-containing product stream and purifying the vitamin E-containing product stream to obtain a purified vitamin E-containing stream which is taken off as a side take-off stream at the take-off section of the first rectification column;
(b) an acetylation stage for acetylating at least a part of the purified vitamin E-containing stream to form a vitamin E acetate (VEA) product stream;
(c) a second rectification column for receiving at least a part of the VEA product stream passed from the acetylation stage to provide as a first grade of VEA product having a purity of ≧97% and/or to provide at least a part of the VEA product stream taken from the acetylation stage a second grade of VEA useful product having a purity of ≧92% by weight;
(d) a third rectification column for receiving a part of the side take-off stream of the first rectification column, optionally together with a part of a distillate stream from an evaporator, to provide a vitamin E-containing useful product having a purity of >97% by weight taken off as either a side or bottom take-off stream from the third rectification column.

4. A system according to claim 3, which further comprises a degassing stage for degassing the vitamin E-containing product stream before the vitamin E-containing product is fed to the first rectification column.

5. A system according to claim 4, wherein the degassing stage comprises a falling-film evaporator.

6. A system according to claim 3, further comprising a short path evaporator for distilling a bottom take-off stream of the second rectification column.

* * * * *